United States Patent [19]

Makovic

[11] Patent Number: 4,492,228

[45] Date of Patent: Jan. 8, 1985

[54] AIR WARMING DEVICE TO FACILITATE BREATHING

[76] Inventor: Edward M. Makovic, 510 N. Lincoln, Coal City, Ill. 60416

[21] Appl. No.: 449,888

[22] Filed: Dec. 16, 1982

[51] Int. Cl.³ ............................................. A61M 15/00
[52] U.S. Cl. ................................................ 128/204.17
[58] Field of Search ...................... 128/204.17, 203.26, 128/201.13

[56] References Cited

U.S. PATENT DOCUMENTS

| | | | |
|---|---|---|---|
| 3,491,754 | 1/1970 | Weese | 128/204.17 |
| 3,707,966 | 1/1973 | Nebel | 128/204.17 |
| 3,902,486 | 9/1975 | Guichard | 128/203.26 |

FOREIGN PATENT DOCUMENTS 8203013  9/1982  European Pat. Off. ........ 128/204.17

*Primary Examiner*—Henry J. Recla
*Assistant Examiner*—Karin M. Reichle
*Attorney, Agent, or Firm*—Ernest Kettelson

[57] ABSTRACT

An air warming device to facilitate breathing comprising a thin wall air warming chamber having a plurality of cells which extend vertically when the device is worn and placed against the chest region of the user. Each cell has a relatively large opening at the bottom and a relatively smaller opening at the upper end. A first manifold extends across the bottom having an upwardly facing open wall in communication with the large openings at the bottom of each cell and having a small opening to admit outside air into the first manifold. A second manifold extends across the top having a downwardly facing open wall in communication with the small openings at the top of each cell, and having a small opening for warmed air to pass from the second manifold through a tube to a breathing mask over the nose of the user. The breathing mask includes an exhaust valve for exhaled air to escape. A layer of insulating material is placed over the outwardly facing wall of the air warming chamber.

9 Claims, 10 Drawing Figures

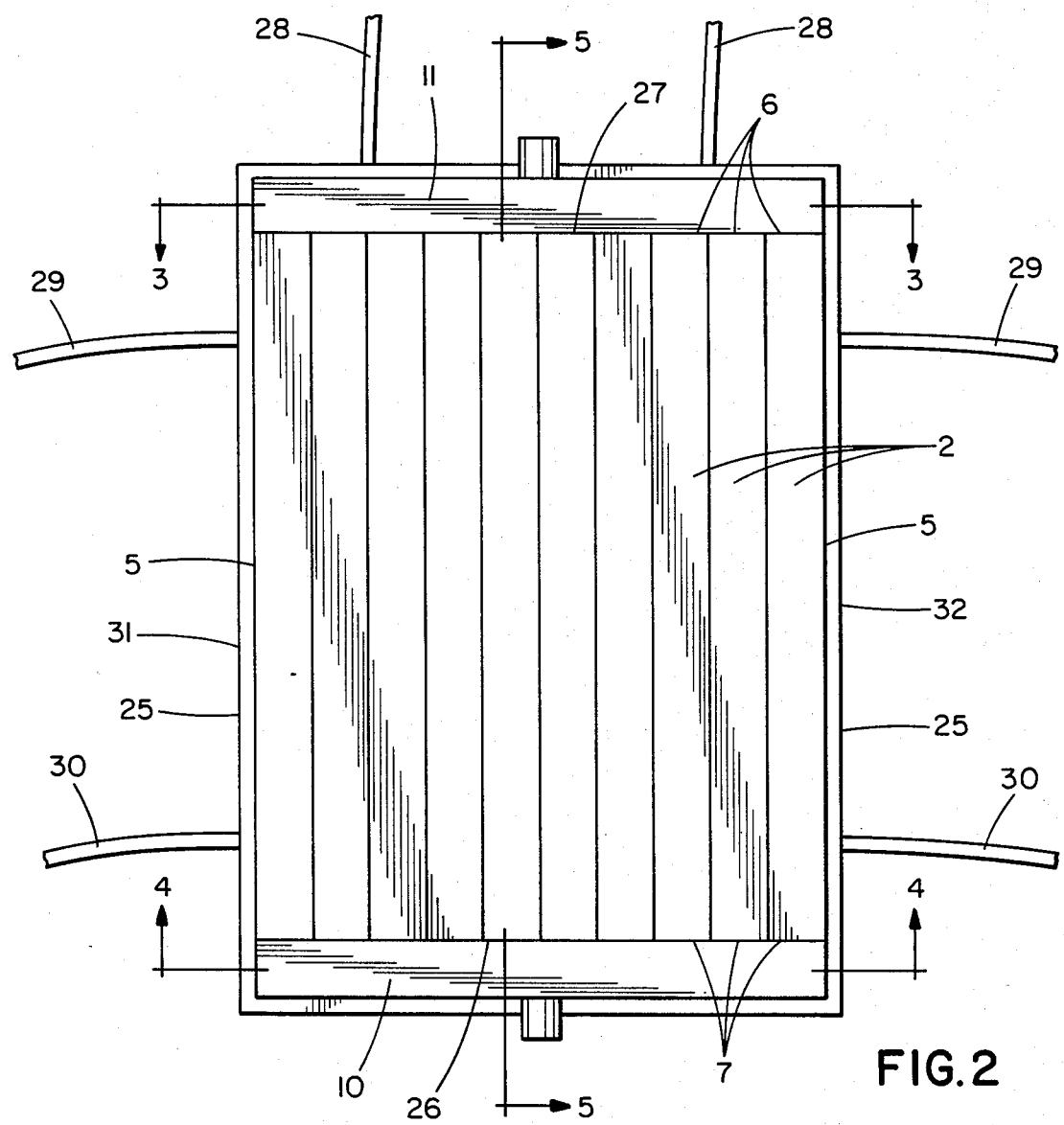

U.S. Patent   Jan. 8, 1985   Sheet 4 of 4   4,492,228 ptions of the invention follow.

AIR WARMING DEVICE TO FACILITATE BREATHING

BACKGROUND OF THE INVENTION

This invention relates to the field of devices for the health and comfort of persons who have difficulty breathing cold air when temperatures fall below freezing or whose health would be jeopardized by breathing cold air at such temperatures.

Many persons who have had heart attacks, or heart bypass operations, and who suffer from other health problems cannot breath cold air at temperatures much below freezing without jeopardizing their health and suffering extreme discomfort. The result is that they must remain indoors most of the time when outside temperatures are below the freezing point. If temperatures become extremely low, such persons have difficulty in venturing outdoors at all. However, if a device were available to warm the outside air which the person could wear as part of his wearing apparel, it would be a relatively simple matter to put such a device on along with warm clothing when they get ready to go outside. If a device of this kind were available which could warm outside air by making use of the user's own body heat, then electrical, mechanical, or chemical means would not be needed to accomplish the heating function. The present invention solves these problems by providing a convenient device which can simply be strapped to the user's chest and the breathing mask placed over the wearer's nose. The cold outside air is then drawn into the warming chamber to provide a supply of warmed air for the user to breathe.

SUMMARY OF THE INVENTION

It is an object of the invention to provide an air warming device to facilitate breathing in which the air is warmed by the user's own body heat.

It is an object of the invention to provide an air warming device to facilitate breathing which does not require electrical, mechanical, or chemical means to accomplish the warming function.

It is an object of the invention to provide an air warming device to facilitate breathing which can be worn by the user under his outer clothing comprising an air warming chamber having a plurality of cells connected to a breathing mask.

It is an object of the invention to provide an air warming device to facilitate breathing which comprises a warming chamber having a plurality of cells, the warming chamber having a relatively large surface area and a relatively shallow depth, the cells which comrpise the warming chamber having relatively large inlet ports and relatively small outlet ports, a first manifold communicating with the inlet ports and a second manifold in communication with the outlet ports of the cells, a single inlet port of said first manifold to admit outside air therein and a single outlet port of said second manifold for discharge of warmed air into a breathing tube connected thereto, said breathing tube being connected to a breathing mask which may be placed over the nose of the user.

BRIEF DESCRIPTION OF THE DRAWING

FIG. 2 is an elevation view from the rear of an air warming device in accordance with this invention.

FIG. 3 is a section view taken on line 3—3 of FIG. 2.

FIG. 4 is a section view taken on line 4—4 of FIG. 2.

DESCRIPTION OF PREFERRED EMBODIMENT

Figure 1:
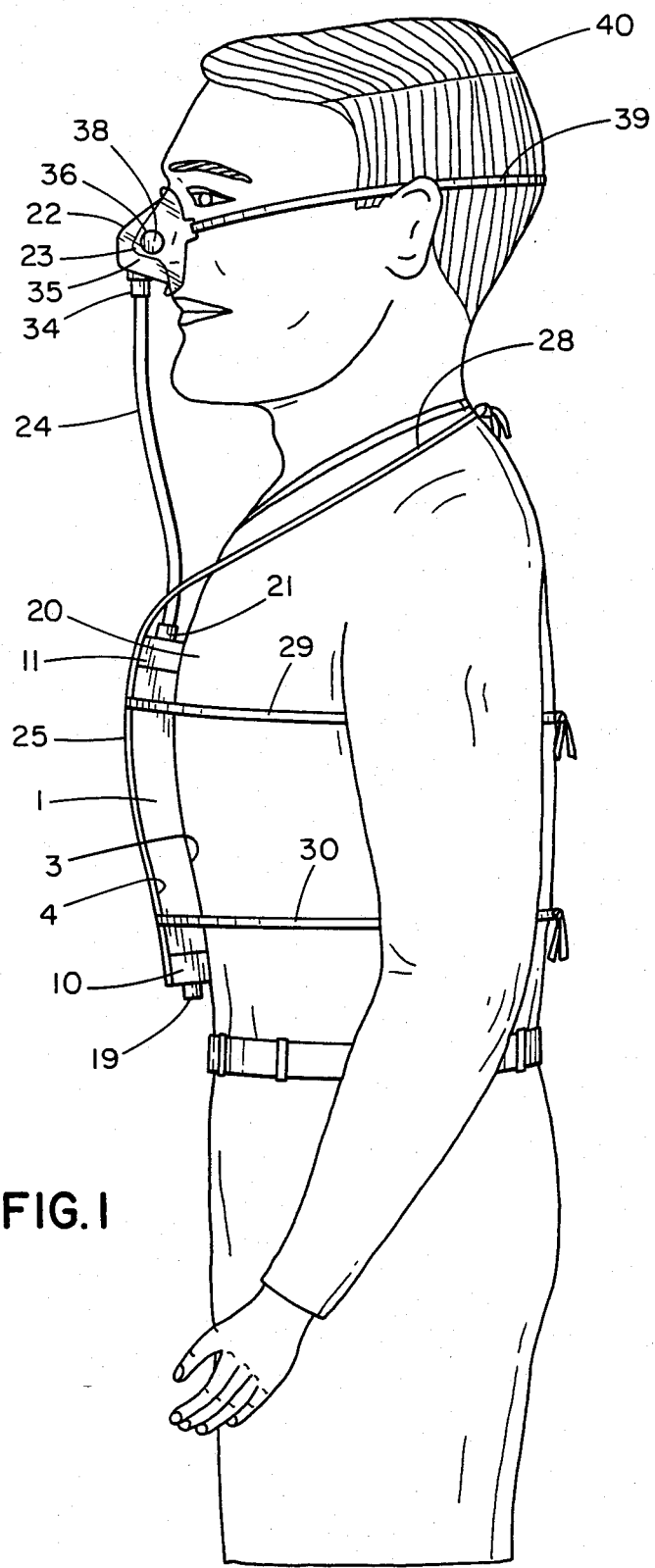
FIG. 1 is a side elevation view of a man wearing an air warming device in accordance with this invention.
Figure 5:
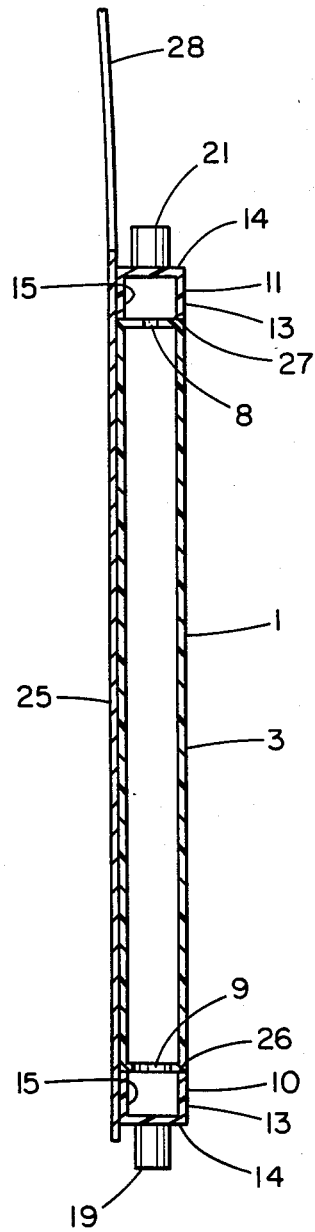
FIG. 5 is a section view taken on line 5—5 of FIG. 2.
Figure 6:
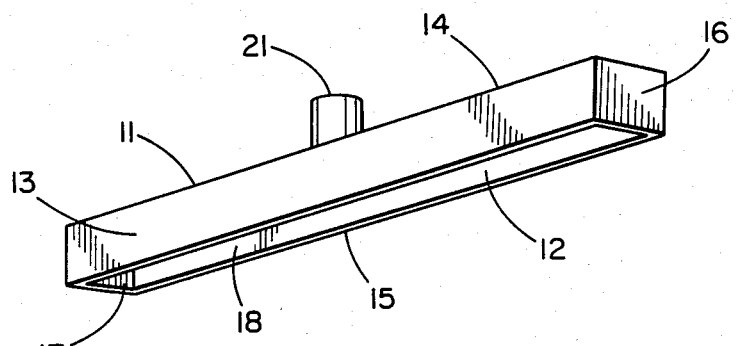
FIG. 6 is a perspective view of the elongated exhaust manifold for use in this invention.
Figure 7:
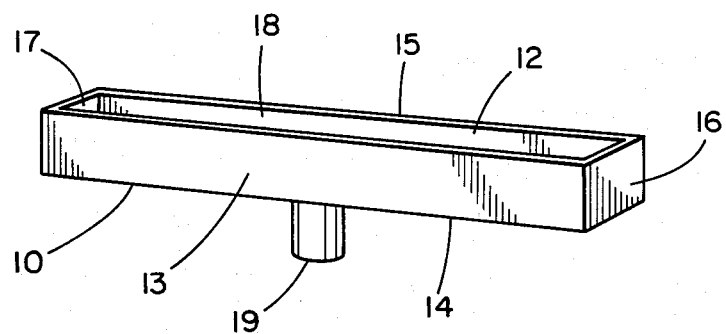
FIG. 7 is a perspective view of the elongated intake manifold for use in this invention.
Figure 8:
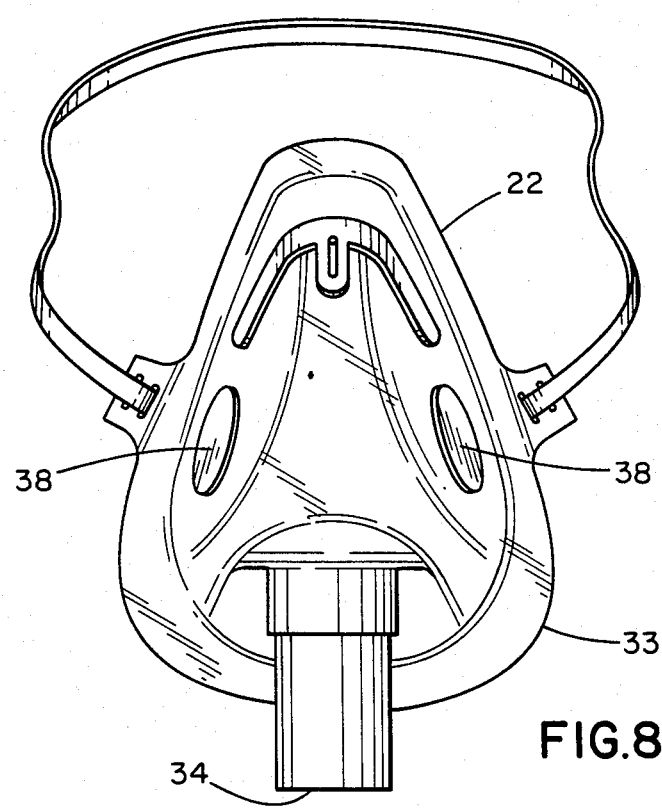
FIG. 8 is an elevation view from the front of a breathing mask for use in this invention.
Figure 9:
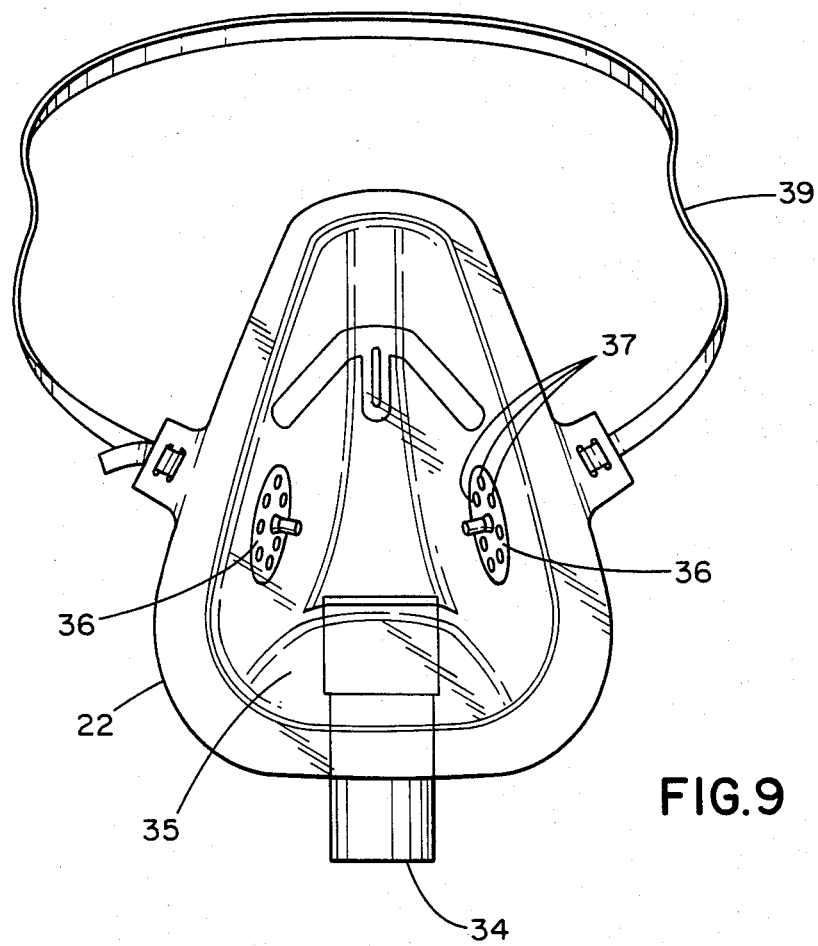
FIG. 9 is an elevation view from the rear of a breathing mask for use in this invention.
Figure 10:
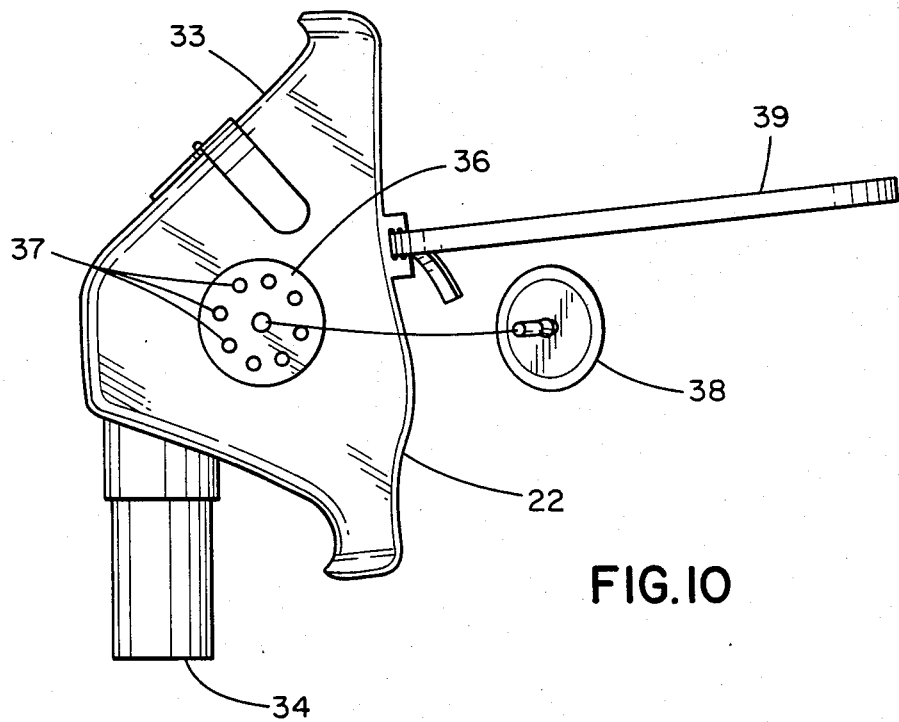
FIG. 10 is an elevation view from the side of a breathing mask for use in this invention.

An air warming device to facilitate breathing in accordance with this invention includes a warming chamber designated by the reference number 1. The warming chamber 1 includes a plurality of elongated cells 2 made of flexible thin wall material which may be rubber or any of the varieties of flexible thin wall plastic materials. The elongated cells 2 are placed in side-by-side relationship to form the warming chamber which thereby has a relatively broad surface area of its inwardly facing wall 3 which will be adjacent to the body of the user when in place and of its outwardly facing wall 4 which faces outwardly in the opposite direction. The depth of the warming chamber is relatively shallow and defined by the side edge walls 5 of the elongated cells 2 which lie at each outer side edge of the warming chamber 1.

By way of example, each of the elongated cells 2 may comprise an elongated rectangular block approximately twelve inches in length and three-fourths of an inch in depth or being three-fourths of an inch square in its cross-sectional dimension. Twelve of these elongated cells 2 can be placed in side-by-side relationship to form a warming chamber 1 which is approximately nine inches wide by twelve inches in length, or nine inches in the horizontal dimension and twelve inches in the vertical dimension when the device is worn by a user to provide a warming chamber which is twelve inches wide in the horizontal dimension, sixteen of the elongated cells 2 may be provided to make up the warming chamber 1. The dimensions of the elongated cells 2 may, of course, be varied as can the number of such elongated cells which make up the warming chamber 1, depending on such things as the size of the person who will be using the device, the degree to which the air is to be warmed and the like.

Each of the elongated cells 2 is substantially square in cross-section having flexible thin wall material bounding a corresponding elongated cavity therein. Each of the elongated cells 2 includes an upper end wall 6 and a lower end wall 7. A relatively smaller discharge opening 8 is formed in the upper end wall 6 of each of the elongated cells 2 and a relatively larger intake opening 9 is formed in the lower end wall 7 of each of the elongated cells 2. The purpose is to provide greater access for cold air from the outside to enter the warming chamber 1 and to provide relatively restricted discharge of air from the warming chamber 1, thereby retaining a quantity of air within the warming chamber to be warmed before it is withdrawn through the discharge openings.

An elongated intake manifold 10 is provided for communication with the intake openings 9 of each of the elongated cells 2 and an elongated exhaust manifold 11 is provided for communication with the discharge openings 8 of the elongated cells 2. The intake manifold 10 and exhaust manifold 11 have substantially the same cross-sectional dimension as the elongated cells 2. The length of each of the manifolds is substantially the same as the width or horizontal dimension of the warming chamber whereby the manifolds extend completely across the upper and lower end walls of the warming chamber to which they are respectively secured. Each manifold includes a chamber 12 bounded by peripheral side walls 13, 14 and 15 which may also be of flexible thin wall material. The chamber 12 of each manifold 10 and 11 is also bounded by end walls 16 and 17 of the same material. Each chamber 12 opens to a completely opened wall 18, the open wall 18 of the intake manifold 10 being in communication with the intake openings 9 of the elongated cells 2 and the open wall 18 of the exhaust manifold 11 being in communication with the discharge openings 8 of the elongated cells 2. An intake port 19 of relatively small dimension is formed in the peripheral side wall 14 of the intake manifold 10 to admit air from the outside into the intake manifold 10 whereupon the air from the outside is distributed to the relatively large intake openings 9 of the elongated cells 2. When the elongated cells 2 are filled with air from the outside, the air is warmed by the body heat of the wearer, the inwardly facing wall 3 of the warming chamber being placed against the chest 20 of the user.

An outlet port 21 is formed in the peripheral side wall 14 of the exhaust manifold 11 to permit warmed air to leave the warming chamber 1 and be carried to a breathing mask 22 placed over the nose 23 of the user through a breathing tube 24 connected at one end to the outlet port 21 of the exhaust manifold 11 and at the other end to the breathing mask 22. When the user inhales, warmed air is drawn from the elongated cells 2 through the relatively smaller discharge openings 8 of the cells 2 through the open wall 18 of the exhaust manifold 11 into its chamber 12 and out through the outlet port 21, then through the breathing tube 24 to the breathing mask 22 where the warmed air is ultimately breathed in by the user.

A sheet of insulating material 25 is secured to the outwardly facing wall 4 of the warming chamber to protect the outwardly facing surface from the cold temperature of the outside and to retain the heat of the warmed air within the elongated cells as it is warmed by the body heat of the user. The sheet of insulating material 25 is large enough to also span the outwardly facing side walls of the manifolds 10 and 11. The sheet of insulating material 25 is preferably bonded directly to the outwardly facing wall of the warming chamber 1 and the outwardly facing walls of the respective intake manifold 10 and exhaust manifold 11. The intake manifold 10 is bonded or otherwise securely connected to the elongated cells 2 of the warming chamber 1 along its lower edge 26 and the exhaust manifold 11 is bonded or otherwise firmly secured along the upper edge 27 of the warming chamber 1. A pair of neck straps 28 are secured at spaced apart locations to the upper edge of the sheet of insulating material 25 which is bonded or otherwise secured to the air warming device. The neck straps 28 extend upwardly and around the back of the neck of the user where they may be tied or fastened to hold the warming chamber 1 in position against the chest 20 of the user. Two pairs of body straps 29 and 30 are secured at spaced apart locations along each opposite side edge 31 and 32 of the sheet of insulating material 25. The pairs of body straps are brought around the back of the user and tied or otherwise fastened behind the user's back to hold the warming chamber 1 close against the chest 20 of the user. The breathing mask 22 includes a peripheral wall 33 of transparent plastic material or other suitable material formed in general to fit over the nose 23 of the user. The breathing mask 22 includes an inlet port 34 connected to the one end of the breathing tube 24 to enable warmed air to enter the cavity 35 of the breathing mask when the user inhales. A pair of exhaust valves 36 are provided in the peripheral wall 33 of the breathing mask to enable air to escape from the cavity 35 of the breathing mask when the user exhales. The exhaust valves include a plurality of port holes 37 opening from the cavity 35 to the outside air. The port holes 37 are covered by flexible discs 38 of rubber or similar flexible material which bear against the port holes to prevent air from escaping from the cavity 35 while the user is inhaling. However, when the user exhales, air pressure from within the cavity 35 through the port holes 37 forces the flexible discs 38 away from the port holes 37 a sufficient distance to enable exhaled air of the user to escape. The breathing mask 22 is held in place over the nose 23 of the user by an elastic strap 39 which extends around the back of the head 40 of the user.

To use the air warming device in accordance with this invention the warming chamber 1 is placed against the chest 20 of the user with the intake manifold 10 facing downwardly and the exhaust manifold 11 facing upwardly, and the neck straps 28 are tied behind the neck of the user. The two pairs of body straps 29 and 30 are tied behind the back of the user to hold the warming chamber 1 securely in place against the chest of the user in order to transmit his body heat through the flexible thin wall of the cells 2 which make up the warming chamber to warm the air which is drawn into the cavity of the cells 2. The breathing mask 22 is placed over the nose 23 of the user with the elastic straps holding the breathing mask 22 in place. The breathing mask 22 is connected to the warming chamber 1 by the breathing tube 24 connected to exhaust manifold 11 which in turn communicates with the elongated cells 2 of the warming chamber 1. The user then puts outer clothing on over the air warming device before going outside. The cold outside air enters the intake manifold 10 through the intake port 19 which opens to the chamber 12 of the intake manifold 10. When the user inhales, warmed air within the elongated cells 2 flows into the exhaust manifold 11 through the breathing tube 24 and breathing mask 22, at the same time cold air is being drawn into the intake manifold 10 where it is distributed to the intake openings 9 at the lower ends of the elongated cells 2. The cold air enters the cavities of the elongated cells 2 through the relatively larger intake openings 9 where the cold air is then retained for a period of time while warmed air in the upper regions of the elongated cells is drawn through the relatively smaller discharge openings 8 into the exhaust manifold 11. The cold air is retained in the cavities of the elongated cells long enough to be warmed by the body heat of the user to a sufficient degree whereby the warmed air is no longer hazardous or harmful to the health of the user. After inhaling warmed air in this manner, the user then exhales and the exhaled air escapes through the port holes 37 of the exhaust valves 36 in the peripheral wall 33 of the breathing mask 22. This process may then be continually repeated for as long as the user desires to remain outdoors, a continuous supply of warmed air being provided as the user continues to inhale and exhale as described.

I claim:

1. An air warming device to facilitate breathing comprising a warming chamber having a peripheral wall comprising a first side wall, a second side wall spaced apart from said first side wall to define warming cavity means therebetween to warm the contents within said cavity means, securing means to secure and hold said warming chamber against a portion of the body of a user, said first side wall being imperforate and adapted for facing the body of said user to transmit body heat from said user to the interior of said warming cavity means, air intake means to admit cold outside air into said warming cavity means, air discharge means to discharge warmed air from said warming cavity means, and air conduit means to conduct said warmed air from said air discharge means to said user to enable said user to breathe said warmed air, wherein said warming cavity means includes a plurality of elongated cells, each of said cells including imperforate side wall means connected between said first and second side walls and surrounding a cavity therein, a first end wall at one end of each of said cells and a second end wall at the opposite end thereof, said air intake means including a relatively large opening in said first end wall of each of said cells to admit cold outside air into said cavity of each of said cells, said air discharge means including a relatively smaller opening in said second end wall of each of said cells to discharge warmed air from said cavity of each of said cells, each smaller opening being substantially aligned with and in substantial registration with a corresponding one of said large openings and in unobstructed open communication therewith.

2. An air warming device to facilitate breathing as set forth in claim 1, wherein said first side wall of said warming chamber includes a relatively broad surface area adapted to face a correspondingly broad body portion of said user to enable transmission of a relatively large amount of body heat from said user to the interior of said warming cavity means, the depth dimension of said warming chamber defined by the space between said first and second side walls being relatively shallow.

3. An air warming device to facilitate breathing as set forth in claim 1, wherein said elongated cells are aligned in a side-by-side array with said first end wall and relatively large opening therein of each of said cells being at a first end of said array, said second end wall and relatively smaller opening therein of each of said cells being at the opposite second end of said array, and wherein said air discharge means also includes an elongated exhaust manifold connected to said warming cavity means and having an exhaust manifold cavity therein positioned adjacent said second end of said array and in fluid communication with said relatively smaller openings in said second end wall of said cells, said exhaust manifold including an outlet from its said cavity, said conduit means being connected to said outlet of said exhaust manifold.

4. An air warming device to facilitate breathing as set forth in claim 3, wherein said air intake means also includes an elongated intake manifold connected to said warming cavity means and having an intake manifold cavity therein positioned adjacent said first end of said array and in fluid communication with said relatively larger openings in said first end wall of said cells, said intake manifold including an intake opening to its said cavity to admit cold outside air therein for distribution to each of said relatively large openings in said first end wall of said cells and entry into each of said elongated cells to be warmed.

5. An air warming device to facilitate breathing as set forth in claim 3, wherein said elongated intake manifold includes a peripheral wall bounding said manifold cavity, said peripheral wall of said cavity being comprised of flexible thin wall sheet material.

6. An air warming device to facilitate breathing as set forth in claim 1, wherein said conduit means includes a breathing mask having a cavity therein, means to secure said mask to said user for fluid communication between the user's nose and said cavity, an inlet port opening to said mask cavity, a breathing tube connected at one end to said inlet port of said mask and at its opposite end to said air discharge means, said breathing mask including exhaust valve means to permit exhaled air from said user to escape to the outside.

7. An air warming device to facilitate breathing as set forth in claim 1, including a sheet of insulating material, said sheet of insulating material secured adjacent said second side wall and adapted to face outwardly away from the body of said user when said air warming device is in place on said user.

8. An air warming device to facilitate breathing as set forth in claim 1, wherein said securing means includes a plurality of straps extending from said warming device for securing around body portions of said user.

9. An air warming device to facilitate breathing as set forth in claim 3, wherein said side wall means of said elongated cells comprises flexible thin wall sheet material.

* * * * *